US007045547B2

(12) United States Patent
Thorpe et al.

(10) Patent No.: US 7,045,547 B2
(45) Date of Patent: May 16, 2006

(54) ACYL-COA DEHYDROGENASE ALLENIC INHIBITORS

(75) Inventors: Colin Thorpe, Newark, DE (US); Wenzhong Wang, Tong'An XiaMen Fujian (CN)

(73) Assignee: University of Delaware, Newark, DE (US)

( * ) Notice: Subject to any disclaimer, the term of this patent is extended or adjusted under 35 U.S.C. 154(b) by 58 days.

(21) Appl. No.: 10/223,385

(22) Filed: Aug. 20, 2002

(65) Prior Publication Data
US 2004/0039032 A1 Feb. 26, 2004

(51) Int. Cl.
*A61K 31/21* (2006.01)
*A61K 31/33* (2006.01)
*C07C 327/00* (2006.01)

(52) U.S. Cl. ............... 514/513; 514/183; 558/250; 558/252; 558/253; 558/254; 558/256

(58) Field of Classification Search ............... 514/513, 514/47, 183; 558/250–256
See application file for complete search history.

(56) References Cited

U.S. PATENT DOCUMENTS

| | | | |
|---|---|---|---|
| 5,051,499 | A | 9/1991 | Shuto et al. |
| 6,110,933 | A | 8/2000 | Takase et al. |
| 6,207,434 | B1 | 3/2001 | Ueda et al. |
| 6,365,628 | B1 | 4/2002 | Berge |
| 6,369,073 | B1 | 4/2002 | Giannessi et al. |

OTHER PUBLICATIONS

Frerman, et al., "Enzyme-Activated Inhibitors, Alternate Substrates, and a Dead End Inhibitor of the General Acyl-CoA Dehydrogenase", The Journal of Biological Chemistry, vol. 255, No. 23, Issue of Dec. 10, pp. 11192-11198 (1980).
Gomes, et al., "Mechanism of Action of Glutaryl-CoA and Butyryl-CoA Dehydrogenases. Purification of Glutaryl-CoA Dehydrogenase", Biochemistry, vol. 20, pp. 1481-1490 (1981).
Fendrich, et al., "Mechanism of Action of Butyryl-CoA Dehydrogenase: Reactions with Acetylenic, Olefinic, and Fluorinated Substrate Analogues", Biochemistry, vol. 21, pp. 6685-6695 (1982).
Powell, et al., "2-Octynol Coenzyme A is a Mechanism-Based Inhibitor of Pig Kidney Medium-Chain Acyl Coenzyme A Dehydrogenase: Isolation of the Target Peptide", Biochemistry, vol. 27, pp. 8022-8028 (1988).
Freund, et al., "Inactivation of General Acyl-CoA Dehydrogenase from Pig Kidney by 2-Alkynoyl Coenzyme A Derivatives: Initial Aspects", Biochemistry, vol. 24, pp. 5996-6002 (1985).
Dakoji, et al., "Redesigning the Active-site of an Acyl-CoA Dehydrogenase: New Evidence Supporting a One-base Mechanism", Bioorganic & Medicinal Chemistry, vol. 5, No. 12, pp. 2157-2164 (1997).
Tanaka, "Jamaican Vomiting Sickness", Handbook of Clinical Neurology, Intoxications of the Nervous System, vol. 37, Part II, Vinken and Bruyn (eds.), North-Holland Publishing Company, Amsterdam, New York, Oxford, pp. 511-539 (1979).
Li, et al., Spiropentylacetyl-CoA, A Mechanism-Based Inactivator of Acyl-CoA Dehydrogenases, J. Am. Chem. Soc., vol. 120, pp. 2008-2017 (1998).
Shin, et al., Cyclobutaneacetyl-CoA: A Janus-Faced Substrate for Acyl-CoA Dehydrogenases, J. Am. Chem. Soc., vol. 116, pp. 8843-8844 (1994).
Cummings, et al., "3-Methyleneoctanoyl-CoA and 3-Methyl-*trans*-2-octenoyl-CoA: Two New Mechanism-Based Inhibitors of Medium Chain Acyl-CoA Dehydrogenase from Pig Kidney", Biochemistry, vol. 33, pp. 788-797 (1994).
Wenz, et al., "Studies with General Acyl-CoA Dehydrogenase from Pig Kidney—Inactivation by a Novel Type of 'Suicide' Inhibitor, 3,4-pentadienoyl-CoA", Eur. J. Biochem, vol. 147, pp. 553-560 (1985).
Lau, et al., "The Reductive Half-Reaction in Acyl-CoA Dehydrogenase from Pig Kidney: Studies with Thiaoctanoyl-CoA and Oxaoctanoyl-CoA Analogues", Biochemistry, vol. 27, pp. 5089-5095 (1988).
Thorpe, et al., "Acyl-Coenzyme A Dehydrogenase from Pig Kidney. Purification and Properties", Biochemistry, vol. 18, No. 2, pp. 331-337 (1979).
Lehman, et al., "An Acyl-Coenzyme A Dehydrogenase Assay Utilizing the Ferricenium Ion", Analytical Biochemistry, vol. 186, pp. 280-284 (1990).

(Continued)

*Primary Examiner*—Shengjun Wang
(74) *Attorney, Agent, or Firm*—Connolly, Bove Lodge & Hutz, LLP

(57) ABSTRACT

Compounds of formula I

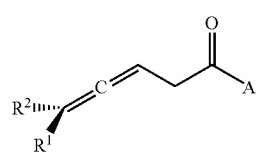

wherein
A is $R^3$, $OR^3$, $SR^3$, and $NR^3R^4$; and $R^1$, $R^2$, $R^3$ and $R^4$ are as defined. The compounds of the invention are reversible inhibitors of acyl-CoA dehydrogenase, and are useful in treating disorders such as diabetes, heart diseases (including angina and congestive heart failure), and peripheral vascular disease in patients suffering from these diseases or conditions resulting thereof.

10 Claims, No Drawings

OTHER PUBLICATIONS

DuPlessis, et al., "Oxidase Activity of the Acyl-CoA Dehydrogenases", Biochemistry, vol. 37, pp. 10469-10477 (1998).

Shamma, et al., "The Synthesis of (±)-Mesembrine", Tetrahedron, vol. 24, pp. 6583-6589 (1968).

Crowley, "Photochemical Formation of Allenes in Solution", Communications to the Editor, Instituto Venezolano de Investigaciones Cientificase (IVIC) Apartado 1827, Carcas, Venezuela, vol. 85, pp. 1210 (1963).

Mori, et al., "Synthesis of Optically Active Forms of Methyl (E)-2,4,5-Tetradecatrienoate, the Pheromone of the Male Dried Bean Beetle", Tetrahedron, vol. 37, pp. 1343-1347 (1981).

Bemert, et al., "An Analysis of Partial Reactions in the Overall Chain Elongation of Saturated and Unsaturated Fatty Acids by Rat Liver Microsomes", The Journal of Biological Chemistry, vol. 252, No. 19, Issue of Oct. 10, pp. 6736-6744 (1977).

Wenzhong Wang et al., Interaction of 3,4-Dienoyl-CoA Thioesters with Medium Chain Acyl-CoA Dehydrogenase: Stereochemistry of Inactivation of a Flavoenzyme, Biochemistry, vol. 40, No. 41, 2001, pp. 12266-12275.

ACYL-CoA DEHYDROGENASE ALLENIC INHIBITORS

GOVERNMENT RIGHTS

The U.S. Government may have rights in this invention as provided for by National Institute of Health (NIH) Grant No. GM26643.

FIELD OF THE INVENTION

This invention is directed to 3,4-dienoyl allene compounds, and their use as inhibitors of acyl-CoA dehydrogenase.

BACKGROUND OF THE INVENTION

Early efforts, e.g., studies with hypoglycin and its analogs, to inhibit or modulate the activity of acyl-CoA dehydrogenases encountered problems of toxicity, and issues related to the generation of irreversible flavin adducts. As a result of these initial studies on acyl-CoA dehydrogenases, efforts and focus turned to other enzymes in the fatty acid oxidation pathway. For example, Etomoxir (for the recovery of glucose oxidation) inhibits carnitine palmitoyltransferase I. Trimetazidine and Ranolazine, are believed to improve cardiovascular performance by partial inhibition of fatty acid oxidation. Trimetazidine inhibits at the level of thiolase—the last enzyme of the beta-oxidation pathway. The target of Ranolazine has yet to be uncovered. Mildronate is another fatty acid oxidation inhibitor under development for heart failure and related ischemic heart disorders. The cellular target of Mildronate is unknown.

Short, medium, long and very long chain acyl-CoA dehydrogenases participate in mitochondrial fatty acid oxidation, with conversion of their straight-chain acyl-CoA substrates to the corresponding enoyl-CoA derivatives. A number of inhibitors of the acyl-CoA dehydrogenases are described in the literature. Both 3- and 2-alkynoyl-CoA derivatives attack the protein moiety of the oxidized enzyme after base-catalyzed abstraction of either α- or γ-protons. See, F. E. Frerman, et al. (1980) *J. Biol. Chem.* 1980, 255, 11192–11928; B. Gomes, et al. in *Biochemistry* 1980, 20, 1481–1490; G. Fendrich, et al. in *Biochemistry* 1982, 21, 6685–6695; C. Thorpe, et al. in *Biochemistry* 1988, 27, 8022–8; C. Thorpe, et al. in *Biochemistry* 1985, 24, 5996–6002; and S. Dakoji, et al. in *Bioorg. Med. Chem.* 1997, 5, 2157–64.

GLU376 is the target of inactivation of the medium chain acyl-CoA dehydrogenase by 2-octynoyl-CoA. GLU376 was confirmed to be the catalytic base by crystallography and mutagenesis. 5,6-Dichloro-4-thia-5-hexenoyl-CoA also inactivates medium-chain dehydrogenase with concomitant covalent modification of GLU376.

Other inhibitors of acyl-CoA dehydrogenase include thioesters that target the flavin prosthetic group of the dehydrogenase yielding an enzyme-bound reduced FAD derivative. One of these, methylenecyclopropylacetyl-CoA (MCPA-CoA), shown as compound 1 in Table 1, is formed during the metabolism of the toxic amino acid methylenecyclopropylalanine (hypoglycin A) found in unripe ackee fruit. See, K. Tanaka, in *Handbook of Clinical Neurology* (Vinken, P. J., Bruyn, C. W., Ed.), pp 511–539, Elsevier, Amsterdam, North Holland 1979. After an initial α-proton abstraction step, MCPA-CoA treatment yields a stable reduced flavin adduct that cannot be reversed by a large excess of normal substrate.

A structurally related compound, spiropentylacetyl-CoA, shown as compound 2 in Table 1, irreversibly inhibits short and medium chain acyl-CoA dehydrogenases through bleaching of the flavin chromophore. See, H. W. Liu et al., in *J. Am. Chem. Soc.* 1988, 120, 2008–2017. The short chain acyl-CoA dehydrogenase is also irreversibly inhibited by another cyclic thioester, cyclobutylacetyl-CoA, with bleaching of the flavin. See, H. W. Liu et al. *J. Am. Chem. Soc.* 1994, 116, 8843–8844.

TABLE 1

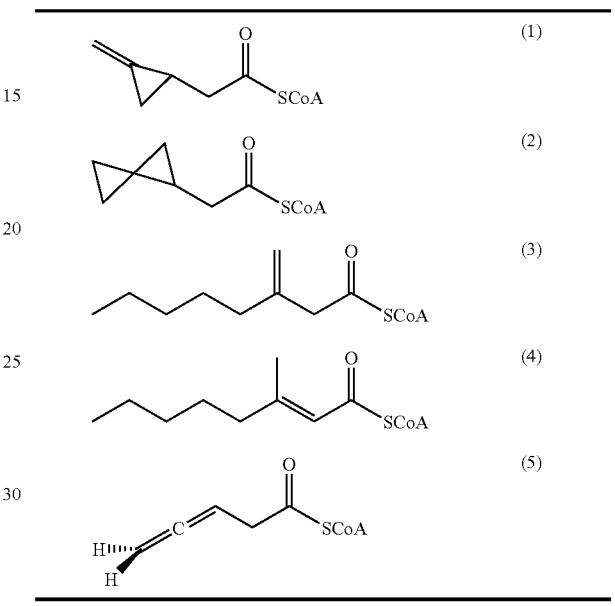

In contrast to these irreversible inhibitors, an interesting class of reversible inhibitors, which form reversible reduced flavin adducts have been reported. See, C. Thorpe, et al. in *Biochemistry* 1994, 33, 788–97. Compounds 3 and 4 shown in Table 1 are activated by α- and γ-proton abstraction, respectively, yet the inhibition proceeds through the same reduced flavin species. Compound 3 is a particularly potent inhibitor.

Ghisla and colleagues observed that addition of 1 equivalent of 3,4-pentadienoyl-CoA, compound 5 in Table 1, leads to rapid reversible formation of a spectrum typical of an N5 reduced flavin adduct. See, C. Thorpe et al., in *Eur. J. Biochem.* 1985, 147, 553–560. This reversible inhibitor targets the flavin prosthetic group of the medium chain dehydrogenase. The compound itself is enzymatically inactive, but activity is achieved by displacing the allene from the oxidized enzyme with the tightly-binding substrate octanoyl-CoA. In the absence of displacing ligand, the reduced flavin adduct decomposes with a half-life of about 75 min, yielding oxidized flavin and the thermodynamically more stable conjugated isomer 2,4-pentadienoyl-CoA.

From a pharmacological perspective, reversible inhibitors are often preferred over irreversible inhibitors because of the relatively lower side effects associated with the former. As a result, it is of interest to provide a novel class of reversible inhibitors of acyl-CoA dehydrogenase.

SUMMARY OF THE INVENTION

The compounds of the invention are reversible inhibitors of acyl-CoA dehydrogenase. The compounds of the invention are of formula I, which include a 3,4-dienoyl allene moiety.

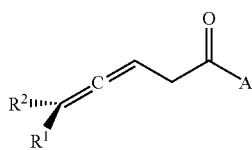

wherein

A is $R^3$, $OR^3$, $SR^3$, and $NR^3R^4$;

$R^1$ is hydrogen, halogen, nitrile, $(C_1–C_4)$alkyl, $(C_2–C_4)$alkenyl, and $(C_2–C_4)$alkynyl, and $(C_3–C_5)$cycloalkyl;

$R^2$ and $R^3$ is independently selected from $(C_1–C_{16})$alkyl, $(C_2–C_{16})$alkenyl, $(C_2–C_{16})$alkynyl, $(C_3–C_{16})$heteroalkyl, $(C_3–C_7)$cycloalkyl and $(C_3–C_7)$heterocycle, and wherein the $(C_1–C_{16})$alkyl, $(C_2–C_{16})$alkenyl, $(C_2–C_{16})$alkynyl, $(C_3–C_{16})$heteroalkyl, $(C_3–C_7)$cycloalkyl and, $(C_3–C_7)$heterocycle is optionally substituted with one or more groups selected from halogen, nitrile, hydroxy, amino, alkoxy, aryl and $(C_3–C_6)$cycloalkyl, wherein $R^1$ and $R^2$ are not the same; and $R^4$ is hydrogen, hydroxyl, $(C_1–C_6)$alkyl, $(C_2–C_6)$alkenyl and $(C_2–C_6)$alkynyl.

DETAILED DESCRIPTION OF THE INVENTION

Because acyl-CoA dehydrogenases catalyze the first committed step in fatty acid oxidation, the enzyme is a target for pharmacological intervention. For example, in disorders such as diabetes, heart diseases (including angina and congestive heart failure), and peripheral vascular disease, e.g., claudication, the diversion of fuel utilization away from fatty acid oxidation towards glucose metabolism has proved to be helpful. In cardiac and peripheral vascular disease this metabolic shift results in a decreased demand for oxygen, improved ionic homeostatis and better cardiac performance. Therefore, it is believed, that partial fatty acid oxidation inhibitors can be used to treat a range of common disorders affecting a very substantial patient base.

In spite of the earlier, unsuccessful attempts to modulate acyl-CoA dehydrogenases Applicants have prepared and identified a family of 3,4-dienoyl allene compounds. The 3,4-dienoyl allene compounds can be used as reversible inhibitors of short-chain, medium-chain, and long chain acyl-CoA dehydrogenase.

The compounds of the invention are reversible inhibitors of acyl-CoA dehydrogenase. The compounds of the invention are of formula I, which include a 3,4-dienoyl allene moiety.

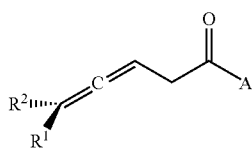

wherein

A is $R^3$, $OR^3$, $SR^3$, and $NR^3R^4$;

$R^1$ is hydrogen, halogen, nitrile, $(C_1–C_4)$alkyl, $(C_2–C_4)$alkenyl, and $(C_2–C_4)$alkynyl, and $(C_3–C_5)$cycloalkyl;

$R^2$ and $R^3$ is independently selected from $(C_1–C_{16})$alkyl, $(C_2–C_{16})$alkenyl, $(C_2–C_{16})$alkynyl, $(C_3–C_{16})$heteroalkyl, $(C_3–C_7)$cycloalkyl and $(C_3–C_7)$heterocycle, and wherein the $(C_1–C_{16})$alkyl, $(C_2–C_{16})$alkenyl, $(C_2–C_{16})$alkynyl, $(C_3–C_{16})$heteroalkyl, $(C_3–C_7)$cycloalkyl and, $(C_3–C_7)$heterocycle is optionally substituted with one or more groups selected from halogen, nitrile, hydroxy, amino, alkoxy, aryl and $(C_3–C_6)$cycloalkyl, wherein $R^1$ and $R^2$ are not the same; and $R^4$ is hydrogen, hydroxyl, $(C_1–C_6)$alkyl, $(C_2–C_6)$alkenyl and $(C_2–C_6)$alkynyl.

Unexpectedly, the degree of reversibility, and hence potency, of the inventive 3,4-dienoyl compounds is dependent on the chain length of $R^2$, and/or the type and position of various optional substituents on $R^2$. In many cases, the characteristic reversibility of the inhibitors of the invention occurs through a slow dehydrogenase-catalyzed isomerization of the 3,4-allene to the non-inhibitory 2,4-diene. In general, the half-life of the inhibitor-enzyme adduct is about 75 min, and results in the regeneration of the oxidized native enzyme.

The reversibility of each respective inventive compound is demonstrated by the return (absorbance) of the oxidized flavin. The reduced flavin adduct decomposes to the 2,4-conjugated diene with the return of the oxidized flavin absorbance spectrum. This isomerization provides a measure of the kinetic stability of each of the enzyme adducts formed. The dehydrogenase enzyme used in the stability testing of the inventive compounds was medium-chain acyl-CoA dehydrogenase (MC-CoA DH) as purified from pig kidney.

The enzyme adduct formed between the compound and MC-CoA DH appears to be more stable with medium chain length allenic inhibitors, that is, with $R^2$ having a chain length between three and five carbons. For example, of the compounds tested for reversible inhibition of MC-CoA DH, 3,4-hexadienoyl-CoA ($C_6$-alleneCoA) forms one of the least stable enzyme adducts, decomposing with a rate constant of 8.7 $hr^{-1}$ at 25° C. In contrast, 3,4-octadienoyl-CoA ($C_8$-alleneCoA) exhibits a relatively more stable enzyme adduct, and has a rate constant of 0.08 $hr^{-1}$. The rate constants for 3,4-pentadienoyl-CoA ($C_5$-alleneCoA), 3,4-heptadienoyl-CoA ($C_7$-alleneCoA), decadienoyl-CoA ($C_{10}$-alleneCoA), 3,4-dodecadienoyl-CoA ($C_{12}$-alleneCoA), and 3,4-pentadecanedienoyl-CoA ($C_{15}$-alleneCoA) were: 1.6 $hr^{-1}$, 1.9 $hr^{-1}$, 0.12 $hr^{-1}$, 0.18 $hr^{-1}$ and 0.27 $hr^{-1}$ respectively.

Extension of the alkyl chain at one of the methylene carbons of the 3–4-dienoyl compounds of the invention creates a new chiral center at the $C_5$-methylene carbon. For example, the stereoisomers, (R)- and (S)-3,4-octadienoyl-CoA, that is, (R)-$C_8$-alleneCoA and (S)-$C_8$-alleneCoA are shown below.

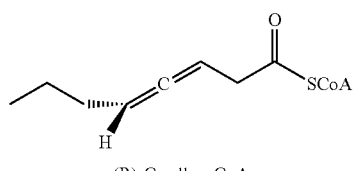

(R)-$C_8$-alleneCoA

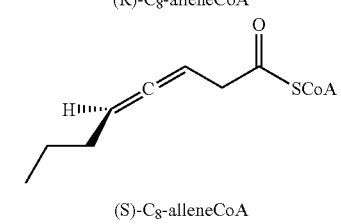

(S)-$C_8$-alleneCoA

Quite surprisingly, the two respective enantiomers are processed very differently by medium chain CoA dehydrogenase. One enantiomer is a potent inhibitor of the dehydrogenase, and the other enantiomer is an isomerase substrate of the enzyme. For example, the (R)-enantiomer of 3,4-octadienoyl-CoA is a potent inhibitor of the dehydrogenase, and the (S)-enantiomer exhibits very little, if any, inhibition of the enzyme. Also, Applicants have observed that even the smallest, i.e., methyl, substituent on the 3,4-pentadienoyl-CoA ($C_6$-alleneCoA) exhibits a relatively high stereoisomeric effect between the two corresponding enantiomers.

A spectral titration with (S)-3,4-decadienoyl-CoA indicates the (S)-enantiomer is a relatively weak inhibitor of the medium chain dehydrogenase, and does not form a detectable flavin adduct. See, Example 1. The (S)-enantiomer is rapidly isomerized to the trans-2,4-conjugated diene. Protein modeling studies suggests that the (S)-enantiomer cannot approach close enough to the isoalloxazine ring to form a flavin adduct, but can be facilely reprotonated by the catalytic base. These structural studies show a surprising, but relatively large, variation in the interaction between structurally similar inhibitors.

Applicants also discovered that the truncation of CoA thioesters can allow the design of unexpectedly potent lipophilic inhibitors of fatty acid oxidation. For example, pantetheine thioesters are unexpectedly more potent inhibitors of the dehydrogenase than the corresponding full-length CoA analog. Thus, the structural alteration of the right hand side of the inventive compounds, that is, that portion of the compound extending from the acyl carbon opposite the allene portion, can also have dramatic influences on the stability of the enzyme adducts, and thus potency.

The truncated version of the compounds of the invention can have the following advantages over similar 3,4-dienoyl compounds with a CoA moiety attached to the acyl carbon:
1. the compounds exhibit an increase in lipophilicity;
2. the compounds can enter mitochondria without the necessity of being activated by carnitine acyltransferase/acyl-CoA synthetase. This avoids the issue of CoA sequestration which affects numerous carboxylic acid-containing compounds.
3. the compounds are, surprisingly, more potent inhibitors of the acyl-CoA dehydrogenase; and
4. the compounds, as a whole, provide a new direction in developing a new generation of hydrolytically stable, lipophilic, pre-activated fatty acid oxidation inhibitors.

The 3,4-dienoyl compounds of the invention exhibit relatively high potency than most known inhibitors of acyl-CoA dehydrogenase. More interestingly, the compounds are not accompanied by an irreversible covalent attachment to the enzyme. Instead, the inhibitor dissociates following isomerization of the allene and activity of the dehydrogenase returns. The reversibility of the inhibitors of the invention avoid issues of immunoreactivity towards the modified enzyme. Also, the reversible nature of the inhibitors minimize the potential for the undesirable accumulation of lipid in tissues. Reversibility also provides advantages associated with pharmacological considerations of safety and dosage.

The dissociation kinetics of the enzyme adducts with the compounds of the invention can be monitored by the release of the conjugated 2,4-diene as a function of both chain length at the methylene carbon of the allene, truncation of the CoA moiety, or the substitution of the CoA moiety with other organic functional groups. The enzyme adducts with (R)-3,4-decadienoyl-pantetheine and (R)-3,4-decadienoyl-N-acetylcysteamine, that is, compounds with a truncated CoA, are 10 and greater than 100 times more stable than the corresponding full length CoA-thioester analog, respectively.

In one embodiment, the compounds of the invention are of formula I, which include a 3,4-dienoyl allene moiety.

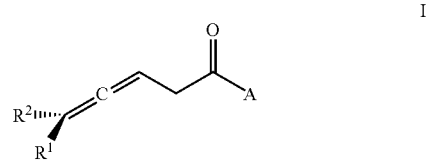

wherein
A is selected from $OR^3$ or $SR^3$;
$R^1$ is hydrogen or methyl;
$R^2$ is ($C_1$–$C_{10}$)alkyl, ($C_2$–$C_{10}$)alkenyl, and ($C_2$–$C_{10}$)alkynyl, ($C_3$–$C_7$)cycloalkyl, and ($C_3$–$C_{10}$)heteroalkyl, and wherein the ($C_1$–$C_{10}$)alkyl, ($C_2$–$C_{10}$)alkenyl, ($C_2$–$C_{10}$)alkynyl, ($C_3$–$C_7$)cycloalkyl, and ($C_3$–$C_{10}$)heteroalkyl is optionally substituted with one or more groups selected from halogen, nitrile, hydroxy, amino, alkoxy, aryl, and ($C_3$–$C_6$) cycloalkyl, wherein $R^1$ and $R^2$ are not the same; and
$R^3$ is independently selected from ($C_1$–$C_{12}$)alkyl, ($C_2$–$C_{12}$)alkenyl, ($C_2$–$C_{12}$)alkynyl, ($C_3$–$C_{12}$)heteroalkyl, ($C_3$–$C_7$)cycloalkyl and ($C_3$–$C_7$)heterocycle, and wherein the ($C_1$–$C_{12}$)alkyl, ($C_2$–$C_{12}$)alkenyl, ($C_2$–$C_{12}$)alkynyl, ($C_3$–$C_{12}$) heteroalkyl, ($C_3$–$C_7$)cycloalkyl and, ($C_3$–$C_7$)heterocycle is optionally substituted with one or more groups selected from halogen, nitrile, hydroxy, amino, alkoxy, aryl and ($C_3$–$C_6$) cycloalkyl, wherein $R^1$ and $R^2$ are not the same.

In another embodiment, the 3,4-dienoyl compounds of the invention can include a class of compounds with A is $XR^3$ of formula II

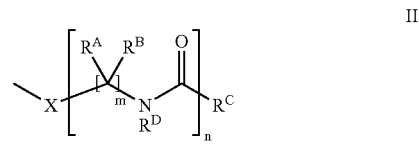

wherein
X is O or S;
$R^A$ and $R^B$ is independently selected from hydrogen, hydroxyl, thiol, nitrile, or ($C_1$–$C_4$)alkyl;
$R^C$ is hydrogen, ($C_1$–$C_{16}$)alkyl, ($C_2$–$C_{16}$)alkenyl, ($C_2$–$C_{16}$)alkynyl, ($C_3$–$C_{16}$)heteroalkyl, ($C_3$–$C_7$)cycloalkyl and ($C_3$–$C_7$)heterocycle, and wherein the ($C_1$–$C_{16}$)alkyl, ($C_2$–$C_{16}$)alkeny ($C_2$–$C_{16}$)alkynyl, ($C_3$–$C_{16}$)heteroalkyl, ($C_3$–$C_7$)cycloalkyl and ($C_3$–$C_7$)heterocycle is optionally substituted with one or more groups selected from halogen, nitrile, hydroxy, amino, alkoxy, aryl and ($C_3$–$C_6$)cycloalkyl;
$R^D$ is selected from hydrogen or ($C_1$–$C_4$)alkyl; and m and n are independently selected from 1, 2, 3, or 4.

A class of compounds of the invention include the pantetheine derivatives of the various $R^1$, $R^2$ substituted 3,4-dienoyl allenes. With respect to formula II, X is S, $R^A$ and $R^B$ is hydrogen, m and n are two, and $R^C$ is a branched heteroalkyl of formula —CH(OH)C($CH_3$)$_2$$CH_2$OH. A compound of the invention is selected from the group consisting of:
(R)- and (S)-3,4-hexadecadienoyl-pantetheine;
(R)- and (S)-3,4-pentadecadienoyl-pantetheine;

(R)- and (S)-3,4-tetradecadienoyl-pantetheine;
(R)- and (S)-3,4-tridecadienoyl-pantetheine;
(R)- and (S)-3,4-dodecadienoyl-pantetheine;
(R)- and (S)-3,4-undecadienoyl-pantetheine;
(R)- and (S)-3,4-decadienoyl-pantetheine;
(R)- and (S)-3,4-nonadienoyl-pantetheine;
(R)- and (S)-3,4-octadienoyl-pantetheine;
(R)- and (S)-3,4-heptadienoyl-pantetheine;
(R)- and (S)-3,4-hexadienoyl-pantetheine; and the respective (R)-stereoisomer of each thereof.

A class of compounds of the invention also include the N-acetylcysteamine derivatives of the various $R^1$, $R^2$ substituted 3,4-dienoyl allenes. With respect to formula II, X is O, $R^A$ and $R^B$ is hydrogen, $R^C$ is ethyl, m is two, and n is one. A compound of the invention is selected from the group consisting of:
(R)- and (S)-3,4-hexadecadienoyl-N-acetylcysteamine;
(R)- and (S)-3,4-pentadecadienoyl-N-acetylcysteamine;
(R)- and (S)-3,4-tetradecadienoyl-N-acetylcysteamine;
(R)- and (S)-3,4-tridecadienoyl-N-acetylcysteamine;
(R)- and (S)-3,4-dodecadienoyl-N-acetylcysteamine;
(R)- and (S)-3,4-undecadienoyl-N-acetylcysteamine;
(R)- and (S)-3,4-decadienoyl-N-acetylcysteamine;
(R)- and (S)-3,4-nonadienoyl-N-acetylcysteamine;
(R)- and (S)-3,4-octadienoyl-N-acetylcysteamine;
(R)- and (S)-3,4-heptadienoyl-N-acetylcysteamine;
(R)- and (S)-3,4-hexadienoyl-N-acetylcysteamine; and the respective (R)-stereoisomer of each thereof.

The compounds of the invention also include various $R^1$, $R^2$ substituted 3,4-dienoyl allenes with CoA-thioester attached to the acyl carbon. A compound of the invention is selected from the group consisting of:
(R)- and (S)-3,4-hexadecadienoyl-CoA;
(R)- and (S)-3,4-pentadecadienoyl-CoA;
(R)- and (S)-3,4-tetradecadienoyl-CoA;
(R)- and (S)-3,4-tridecadienoyl-CoA;
(R)- and (S)-3,4-dodecadienoyl-CoA;
(R)- and (S)-3,4-undecadienoyl-CoA;
(R)- and (S)-3,4-decadienoyl-CoA;
(R)- and (S)-3,4-nonadienoyl-CoA;
(R)- and (S)-3,4-octadienoyl-CoA;
(R)- and (S)-3,4-heptadienoyl-CoA;
(R)- and (S)-3,4-hexadienoyl-CoA; and the respective (R)-stereoisomer of each thereof.

A class of compounds of the invention also include glycerol ester and derivatives thereof of the various $R^1$, $R^2$ substituted 3,4-dienoyl allenes.

A class of compounds of the invention also include carnitine ester and derivatives thereof of the various $R^1$, $R^2$ substituted 3,4-dienoyl allenes.

In many instances, the compounds of the invention are reversible inhibitors of acyl-CoA dehydrogenase.

The term "alkyl" refers to an optionally substituted straight-chain or branched-chain hydrocarbon radical. Examples of alkyl radical include methyl, ethyl, n-propyl, isopropyl, n-butyl, isobutyl, sec-butyl, tert-butyl, pentyl, and the like.

The term "alkenyl" refers to a straight-chain or branched-chain hydrocarbon radical having one or more carbon-carbon double bonds. Examples of alkenyl radicals include ethenyl, propenyl, 1,4-butadienyl and the like.

The term "alkynyl" refers to a straight-chain or branched-chain hydrocarbon radical having one or more carbon-carbon triple bonds. Examples of alkenyl radicals include ethynyl, propynyl, butynyl and the like.

The term "aryl" refers to optionally substituted aromatic ring systems. The term "aryl" also includes bicyclic groups in which the aromatic ring is fused to a heterocyclic ring, a cyclohexane ring, a heteroaryl ring, or another benzene ring.

The term "heteroalkyl" refers to an optionally substituted straight-chain or branched-chain hydrocarbon radical with one or more atoms selected from nitrogen, oxygen, or sulfur. Examples of heteroalkyl radicals include one or more functional groups selected from esters, ethers, thioethers, amine, amides, thiols, alcohols, ketones, and the like. Preferred heteroalkyls include one or more amide groups or one or more hydroxyl groups. Example of some preferred heteroalkyls include pantetheine, N-acetylcysteamine, carnitine, and glycerol.

The term "heteroaryl" refers to optionally substituted aromatic ring systems having one or more heteroatoms selected from oxygen, nitrogen and sulfur. The term heteroaryl also includes bicyclic groups in which the heteroaryl ring is fused to a benzene ring, heterocyclic ring, a cyclohexane ring, or another heteroaryl ring. The term heteroaryl includes ring systems such as, for example, pyridine, quinoline, furan, thiophene, pyrrole, imidazole and pyrazole.

The term "alkoxy" refers to an alkyl ether radical wherein the term alkyl is defined as above. Examples of alkoxy radicals include methoxy, ethoxy, n-propoxy, isopropoxy, n-butoxy, iso-butoxy, sec-butoxy, tert-butoxy and the like.

The term "cycloalkyl" refers to a saturated or partially saturated monocyclic, bicyclic or tricyclic alkyl radical wherein each cyclic moiety has about 3 to about 8 carbon atoms. Examples of cyclcoalkyl radicals include cyclopropyl, cyclobutyl, cyclopentyl, cyclohexyl and the like.

The term "heterocycle" or "heterocyclic ring" refers to any 3- or 4-membered ring containing a heteroatom selected from oxygen, nitrogen and sulfur; or a 5-, 6- or 7-membered ring containing one, two or three nitrogen atoms; one oxygen atom; one sulfur atom; one nitrogen and one sulfur atom; one nitrogen and one oxygen atom; two oxygen atoms in non-adjacent positions; one oxygen and one sulfur atom in non-adjacent positions; or two sulfur atoms in non-adjacent positions. The 5-membered ring has 0-2 double bonds and the 6- and 7-membered rings have 0–3 double bonds. The term "heterocyclic" also includes bicyclic groups in which any of the above heterocyclic rings is fused to a benzene ring, a cyclohexane ring or another heterocyclic ring (for example, indolyl, quinolyl, isoquinolyl, tetrahydroquinolyl, benzofuryl, dihydrobenzofuryl or benzothienyl and the like). Heterocyclics include: pyrrolyl, pyrazolyl, imidazolyl, morpholinyl, indolyl, quinolinyl, and thienyl.

The pharmaceutical compositions of this invention can be used in the form of a pharmaceutical preparation, for example, in solid, semisolid, liquid or aerosol form which contains one or more of the compounds of the invention, as an active ingredient, in admixture with an organic carrier, inorganic carrier, or excipient suitable for external, enteral or parenteral applications. The active ingredient may be compounded, for example, with the usual nontoxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The compound is included in the pharmaceutical composition in an amount sufficient to produce the desired effect upon the process or condition of diseases.

In a number if disease states (including diabetes and angina) modulation of the utilization of fatty acid as metabolic fuel is beneficial. The reversible mode of inhibition of the inventive compounds provides for flexibility, and the nature of their mode of action provides for high specificity and tunable lipophilicity and enzymatic potency.

For the treatment of diabetes, cardiovascular and peripheral vascular diseases (such as angina, congestive heart failure and claudication), the compounds of the invention can be administered orally, topically, parenterally, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

Dosage levels of the compounds of the invention are of the order from about 0.005 mg to about 50 mg per kilogram of body weight per day, preferably from about 0.1 mg to about 10 mg per kilogram of body weight per day, are useful in the treatment of the above-indicated conditions (from about 0.7 mg to about 3.5 g per patient per day, assuming a 70 kg patient). In addition, the compounds of the present invention may be administered on an intermittent basis; i.e. at daily, semiweekly, weekly, semi-monthly or monthly intervals.

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material that can vary from about 5 to about 95 percent of the total composition. Dosage unit forms will generally contain from about 0.5 mg to about 500 mg of active ingredient, and preferably about 0.5 mg to about 100 mg of active ingredient. For external administration the compound of can be formulated within the range of, for example, 0.0001% to 60% by weight, preferably from 0.001 to 10% by weight, and most preferably from about 0.005 to 0.8% by weight.

The following examples are given for the purpose of illustrating the compounds of the invention and shall not be construed as being limitations on the scope or spirit of the instant invention.

EXAMPLES

General Information: Medium chain acyl-CoA dehydrogenase was purified from pig kidney as described previously (33). Porcine liver esterase (EC 3.1.1.1), CoASH (lithium salt), D-pantethine, and 5,5'-dithio-bis(2-nitrobenzoic acid) were obtained from Sigma. E,E-2,4-octadienal and E,E-2,4-dodecadienal were from Alfa and K & K Laboratories respectively. All concentrations of dehydrogenase enzyme refer to active sites using an extinction coefficient of 15.4 $mM^{-1} cm^{-1}$ at 446 nm as demonstrated in C. Thorpe et al. in *Biochemistry* 1979, 18, 331–337. Unless otherwise stated, buffers were 50 mM potassium phosphate, pH 7.6, containing 0.3 mM EDTA, and experiments were conducted at 25° C. Assays of the medium chain dehydrogenase were as described previously, see C. Thorpe et al. in *Anal. Biochem.* 1990, 186, 280–284. Static and rapid-reaction spectrophotometry were performed as reported in C. Thorpe et al, in *Biochemistry* 1998, 37, 10469–10477.

Example 1

Synthesis of Racemic 3,4-dienoic Acids

Dienals are oxidized by silver oxide to provide the corresponding dienoic acids as previously described (H. R. Rodriguez, et al. in *Tetrahedron* 1968, 24, 6583–6589). The resulting acids are photo-isomerized with a Hanovia L 450-W high-pressure mercury lamp to provide racemic 3,4-dienoic acids as previously described (K. J. Crowley in *J. Amer. Chem. Soc.* 1963, 85, 1210).

Example 2

Synthesis of Chiral 3,4-decadienoic Acids

Alternatively, methyl esters can be synthesized from racemic precursors by the orthoester Claisen rearrangement as described by T. Ebata et al., in *Tetrahedron* 1981, 37, 1343–1347. R(−)- and S(+)-1-octyn-3-ols are the precursors for R(−)- and S(+)- methyl decadienoates respectively (39). Each octynol (1.0 g) was mixed with propionic acid (40 mg) and trimethylorthoacetate (7.6 g) and refluxed under nitrogen at 105° C. for 6 h. After completion of the reaction (TLC: using methanol:ethylacetate 1/1 v/v; detection by iodine vapor) excess trimethylorthoacetate is removed by distillation at 120° C. The residue (1.68 g) is stirred for 30 min with 2 mL of 0.5 M $H_2SO_4$ and extracted with three 5 mL aliquots of ether. The extract is dried over anhydrous magnesium sulfate and the ether removed under reduced pressure to provide 1.30 g of a pale yellow liquid. $\delta^H H$ ($CDCl_3$): -O-methyl, 3.75 ppm (s, 3H); C-2, 3.02 ppm (m, 2H); C-3 and C-5, 5.20 ppm (br, 2H); C-6, 1.95ppm (m, 2H), and C-7,-8 and -9, 1.2–1.4 ppm (br, 6H). The optical rotations for R(−)- and S(+)- methyl esters in diethylether are $[\alpha]^{22}_D$ −37.3° and +38.2° respectively. A portion of the ester (0.45 g) is hydrolyzed by 200 units of porcine liver esterase in 30 mL of 250 mM phosphate buffer, pH 7.0. The mixture is stirred vigorously at room temperature for 72 h in a closed flask under nitrogen, then acidified to pH 2 with HCl, and finally extracted with three 15 mL aliquots of ether. The extractions are pooled and the ether removed under reduced pressure. The residue is washed with three 15 mL aliquots of 250 mM sodium bicarbonate solution (pH adjusted to 8.), and un-hydrolyzed ester removed by extractions with ether. The aqueous layer is brought to pH 2 with HCl and extracted with ether as before. The extracts are dried and the ether removed under reduced pressure to provide 0.15 g of the acid. The acid compounds exhibit $[\alpha]^{22}_D$=−57.7° and +60.1° for R- and S-isomers respectively.

Example 3

Preparation of 3,4-allenic Thioesters

The allenoyl CoA thioesters are synthesized by the mixed anhydride method as described previously (H. Sprecher et al. in *J. Biol. Chem.* 1977, 252, 6736–6744) with minor modifications. 36.3 μmol allenic acid, 36.3 μmol isobutylchloroformate and 33.0 μmol of dry triethylamine are mixed in 2.0 mL dry tetrahydrofuran and stirred for 10 min at room temperature. CoASH (24.2 μmol in 1.5 mL of 250 mM phosphate buffer, pH 8.2) is added and the mixture stirred under nitrogen for 20 min. The solution is acidified to pH 5 with glacial acetic acid and the mixture extracted with ether. The remaining aqueous layer is purified by HPLC. A shallow gradient of methanol and 25 mM potassium phosphate, pH 5.3, is used to resolve the 3,4-allene from a small amount of 2,4-dienoyl-CoA contaminant. A typical elution program for 3,4-decadienoyl-CoA is: 1.5 min, phosphate buffer alone; 1.5–3.5 min, linear gradient to 65% methanol; 3.5–12 min, linear gradient to 66% methanol; 12–15 min, linear gradient to 80% methanol; 15–20 min, linear gradient to 100% phosphate buffer. The 3,4-decadienoyl-CoA eluted at 13.7 min. The gradient was tailored to the varying chain lengths of thioesters synthesized in this work. All resulting 3,4-allenic CoA thioesters are quantitated using an extinction coefficient of 16 $mM^{-1}$ $cm^{-1}$ at 260 nm.

Example 4

The procedures of Example 3 are adapted to synthesize the corresponding 3,4-decadienoyl pantetheine and 3,4-decadienoyl N-acetylcysteamine thioesters. The pantetheine derivative is prepared using sodium borohydride reduction of D-pantethine as previously described (R. H. Abeles et al., in *Biochemistry* 1981, 20, 1481–1490) The reaction is quenched with acetone, and the pH carefully adjusted to 8.2. The reduced preparation is stored in aliquots at −70° C. and standardized with 5,5'-dithio-bis(2-nitrobenzoic acid) (DTNB) before use. With either the pantetheine or N-acetylcysteamine derivative, the thioesterification reaction mixture is not adjusted to pH 5.3, but extracted with three 4 mL ether aliquots. The extracts are combined, dried over anhydrous magnesium sulfate and the solvent removed under reduced pressure. The thioesters are dissolved in 20% acetonitrile and purified by HPLC using a water/acetonitrile gradient followed at 234 nm. Both compounds are quantitated using an extinction coefficient of 3.8 $mM^{-1}$ $cm^{-1}$.

Example 5

Synthesis and Evaluation of R-(−)- and S-(+)-3,4-decadienoyl-CoA

R- and S-3,4-decadienoyl-CoA are prepared by first synthesizing the corresponding methyl decadienoates using the orthoester Claisen rearrangement starting with commercially available R- or S-1-octyn-3-ol. Enzymatic hydrolysis of the methyl ester gave the R- and S-acids which were converted to the CoA thioester by the mixed anhydride method and purified by HPLC.

Conventional steady-state turnover experiments to evaluate the rate at which the (S)-enantiomer is converted to the 2,4-diene are complicated by the presence of about 5% of the inhibitory (R)-enantiomer. The reaction is therefore followed at high enzyme concentrations in a stopped-flow spectrophotometer. 2,4-Diene formation is monitored at 312 nm. Although the absorbance traces at 312 nm are markedly curved, slopes recorded between 3 and 50 msec suggest a turnover number of about 6 $s^{-1}$ at 2° C. for the (S)-enantiomer. The interaction between the dehydrogenase and the purified (R)-enantiomer is significantly faster. Hence, incubation with an excess of the racemate results in rapid inactivation of the enzyme by the (R)-enantiomer before much isomerization of (S)-enantiomer can occur.

Example 6

Enzyme Adduct Formation with R-(−)-3,4-decadienoyl-pantetheine and R-(−)-3,4decadienoyl-N-acetylcysteamine.

The pantetheine thioester and N-acetylcysteamine thioester compounds exhibit essentially the same spectral changes and stoichiometry as shown in FIG. 1B. Bleaching of the flavin chromophore, followed at 446 nm, is relatively rapid for the pantetheine compound, but slow enough for a conventional spectrophotometer with the N-acetylcysteamine compound. At 50 μM, the rate constants are 30.9 $s^{-1}$, 7.5 $s^{-1}$, and 0.035 $s^{-1}$ for the CoA, pantetheine, N-acetylcysteamine compounds, respectively at 2° C. Limiting rates of 33 $s^{-1}$ and 55 $s^{-1}$ are obtained for CoA and pantetheine thioesters, respectively. A corresponding maximal limiting rate for the N-acetylcysteamine compounds could not be obtained because of the low solubility of this compound. Clearly, the CoA thioester is most effective at low concentration, although the limiting rate for pantetheine is about 1.6 times that of CoA. The pantetheine compound (at 50 μM) exhibits a long wavelength band one quarter as intense as that observed with the CoA compound. In contrast, no long-wavelength band was observed with R-(−)-3,4-decadienoyl-N-acetyl-cysteamine and reduction of the enzyme was extremely slow.

Example 7

Adduct Formation with R-3,4-decadienoyl-CoA

Dehydrogenase and R-(−)3,4-decadienoyl-CoA are mixed in the stopped-flow spectrophotometer at 2° C. to give final concentrations of 11 μM and 60 μM. The absorbance changes at 446 and 800 nm are shown in the inset of FIG. 2. As is observed with a number of diverse thioester substrates, such as butyryl-, octanoyl- and dihydrocinnamoyl-CoA, bleaching of the flavin at 446 nm is biphasic. The main panel in FIG. 2 shows initial and final spectra from this stopped-flow experiment, together with a spectrum at 20 ms that is constructed from individual wavelength scans. This intermediate species has a broad long-wavelength absorbance maximal at about 800 nm with a significantly skewed residual oxidized flavin component.

Example 8

Kinetic Stability of Adducts Formed Between 3,4-dienoyl-CoA Compounds

A solution of acyl-CoA dehydrogenase (9.5 μM in 50 mM phosphate buffer, pH 7.6, 25° C.) is mixed with 1.6 equivalents of racemic 3,4-dienoyl-CoA derivatives (0.8 equivalent of R-isomer) containing 5, 6, 7, 8, 10, 12 and 15 carbon acyl chains. The return of oxidized flavin absorbance was monitored at 446 nm. A sub-stoichiometric amount (1.6 equivalents racemate: corresponding to 0.8 equivalent of the R-isomer) is used to avoid the lag phases encountered in the presence of excess inhibitor. The return of oxidized flavin absorbance is strongly chain length dependent.

FIG. 1 shows the spectrophotometric titrations of medium chain acyl-CoA dehydrogenase with racemic, R-(−)- and S-(+)-3,4-octadienoyl-CoA. As shown in FIG. 1A, acyl-CoA dehydrogenase (9.7 μM in 50 mM phosphate buffer, pH 7.6, 25° C.; curve 1) was titrated with 5.7, 11.3, 16.9, and 20.6 μM of racemic 3,4-octadienoyl-CoA (curves 2–5 respectively). The spectral changes were completed rapidly before measurement could be made. Intermediate spectra are omitted for clarity. The inset shows the stoichiometry of bleaching at 446 nm. As shown in FIG. 1B, the enzyme (9.6 μM in 50 mM phosphate buffer, pH 7.6, 25° C.; curve 1) was titrated with 1.68, 3.36, 5.05, 6.72, 8.41, 16.8 μM of R-(−)-decadienoyl-CoA (Curves 2–7, respectively). The inset shows the 446 nm absorbance versus equivalents of the allenic compound added at 0.95 equivalents. In FIG. 1C, the enzyme (5.06 μM in 50 mM phosphate buffer, pH 7.6, 25° C.; curve 1) was titrated with 2.53, 5.06, 36.4, 66.8, 109.3 μM of S-(+)-decadienoyl-CoA (curves 2–6, respectively).

Intermediate spectra are omitted for clarity. The absorbance values at 446 nm are shown in the inset.

FIG. 2 shows the intermediates in the reduction of the medium chain acyl-CoA dehydrogenase by R-(−)-3,4-decadienoyl-CoA. The absorbance changes were recorded in a 2 cm path-length cell after mixing dehydrogenase and R-(−)-thioester in the stopped flow spectrophotometer to give final concentrations of 5.5 and 30 μM respectively in 50 mM phosphate buffer, pH 7.6 at 2° C. The inset shows the absorbance time course at 446 and 800 nm (curves a and b, respectively). Absorbance traces at a range of wavelengths were used to construct the spectrum of the intermediate species maximal at about 20 msec.

Example 9

Enzyme adduct stabilities with the medium-chain acyl-CoA dehydrogenase of R-(−)-3,4-decadienoyl-CoA, R-(−)-3,4-decadienoyl-pantetheine, and R-(−)-3,4-decadienoyl N-acetylcysteamine were compared. The dehydrogenase was incubated with 0.8 equivalents of the CoA, pantetheine and N-acetylcysteamine thioesters of R-(−)-3,4-decadienoic acid until maximal bleaching of the flavin chromophore was observed. The reappearance of the oxidized flavin chromophore was then followed at 25° C. The CoA adduct was the least stable, with a half-life of 5.6 hours. The pantetheine adduct was almost 9 times more stable, and the N-acetylcysteamine adduct was the most stable of all, with no appreciable regain of the flavin absorbance after two days.

Example 10

In competition studies with the substrate octanoyl-CoA, at a concentration of 30 μM, both the CoA and pantetheine analogs of the compounds of the invention are shown to be relatively strong reversible inhibitors of medium chain dehydrogenase. The assay studies included a dehydrogenase concentration of 3 nM. Compared to a control without inhibitor, 4.4 nM of the 3,4-decadienoyl-CoA analog decreased the rate to 50% within 1 minute. The corresponding pantetheine analog required 0.5 μM, which is still significantly lower than the 30 μM concentration of the substrate in the assay.

We claim:

1. A compound of formula I, which includes a 3,4-dienoyl allene moiety of formula I

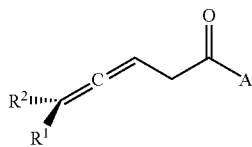

I wherein
A is SR³;
R¹ is hydrogen, halogen, nitrile, (C₁–C₄)alkyl, (C₂–C₄)alkenyl, and (C₂–C₄alkynyl, and (C₃–C₅)cycloalkyl;
R² and R³ is independently selected from (C₁–C₁₆)alkyl, (C₂–C₁₆)alkenyl, (C₂–C₁₆)alkynyl, (C₃–C₁₆)heteroalkyl, (C₃–C₇)cycloalkyl and (C₃–C₇)heterocycle, and wherein the (C₁–C₁₆)alkyl, (C₂–C₁₆)alkenyl, (C₂–C₁₆)alkynyl, (C₃–C₁₆)heteroalkyl, (C₃–C₇)cycloalkyl and (C₃–C₇)heterocycle is optionally substituted with one or more groups selected from halogen, nitrile, hydroxy, amino, alkoxy, aryl and (C₃–C₆)cycloalkyl, wherein R¹ and R² are not the same.

2. The compound of claim 1 wherein A is pantetheine.
3. The compound of claim 1 wherein A is N-acetylcysteamine.
4. A compound of claim 2 selected from the group consisting of:
(R)- and (S)-3,4-hexadecadienoyl-pantetheine;
(R)- and (S)-3,4-pentadecadienoyl-pantetheine;
(R)- and (S)-3,4-tetradecadienoyl-pantetheine;
(R)- and (S)-3,4-tridecadienoyl-pantetheine;
(R)- and (S)-3,4-dodecadienoyl-pantetheine;
(R)- and (S)-3,4-undecadienoyl-pantetheine;
(R)- and (S)-3,4-decadienoyl-pantetheine;
(R)- and (S)-3,4-nonadienoyl-pantetheine;
(R)- and (S)-3,4-octadienoyl-pantetheine;
(R)- and (S)-3,4-heptadienoyl-pantetheine;
(R)- and (S)-3,4-hexadienoyl-pantetheine; and the respective (R)-stereoisomer of each thereof.

5. A compound of claim 3 selected from the group consisting of:
(R)- and (S)-3,4-hexadecadienoyl-N-acetylcysteamine;
(R)- and (S)-3,4-pentadecadienoyl-N-acetylcysteamine;
(R)- and (S)-3,4-tetradecadienoyl-N-acetylcysteamine;
(R)- and (S)-3,4-tridecadienoyl-N-acetylcysteamine;
(R)- and (S)-3,4-dodecadienoyl-N-acetylcysteamine;
(R)- and (S)-3,4-undecadienoyl-N-acetylcysteamine;
(R)- and (S)-3,4-decadienoyl-N-acetylcysteamine;
(R)- and (S)-3,4-nonadienoyl-N-acetylcysteamine;
(R)- and (S)-3,4-octadienoyl-N-acetylcysteamine;
(R)- and (S)-3,4-heptadienoyl-N-acetylcysteamine;
(R)- and (S)-3,4-hexadienoyl-N-acetylcysteamine; and the respective (R)-stereoisomer of each thereof.

6. The compound of claim 1 wherein R₃ is a (C₃–C₁₆) heteroalkyl.

7. A compound of formula

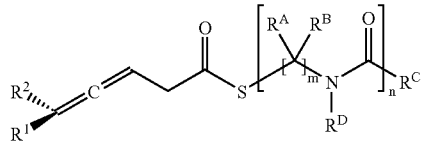

wherein
R^A and R^B is independently selected from hydrogen, hydroxyl, thiol, nitrile, or (C₁–C₄alkyl;
R_C is hydrogen, (C₁–C₁₆)alkyl, (C₂–C₁₆)alkenyl, (C₂–C₁₆)alkynyl, (C₃–C₁₆)heteroalkyl, (C₃–C₇)cycloalkyl and (C₃–C₇)heterocycle, and wherein the (C₁–C₁₆)alkyl, (C₂–C₁₆)alkenyl, (C₂–C₁₆)alkynyl, (C₃–C₁₆)heteroalkyl, (C₃–C₇)cycloalkyl and (C₃–C₇) heterocycle is optionally substituted with one or more groups selected from halogen, nitrile, hydroxy, amino, alkoxy, aryl and (C₃–C₆)cycloalkyl;
R^D is selected from hydrogen or (C₁–C₄)alkyl; and m and n are independently selected from 1, 2, 3, or 4.

8. The compound of claim 6 wherein R^A and R^B is hydrogen.

9. A pharmaceutical composition for inhibiting acyl-CoA-dehydrogenase in a mammal comprising a compound according to claim 1 and a pharmaceutically acceptable carrier.

10. A pharmaceutical composition for inhibiting acyl-CoA-dehydrogenase in a mammal comprising a compound according to claim 7 and a pharmaceutically acceptable carrier.

* * * * *